(12) United States Patent
Buchanan et al.

(10) Patent No.: US 12,186,574 B2
(45) Date of Patent: *Jan. 7, 2025

(54) WCD MONITOR SUPPORTING SERVICEABILITY AND REPROCESSING

(71) Applicant: West Affum Holdings DAC, Dublin (IE)

(72) Inventors: Robert R. Buchanan, Bothell, WA (US); Quan H. Nguyen, Renton, WA (US); Allison Staheli, Bothell, WA (US); Larry J. Spyridis, Seattle, WA (US); Rachel G. Taylor, Marysville, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/502,474

(22) Filed: Nov. 6, 2023

(65) Prior Publication Data

US 2024/0075307 A1 Mar. 7, 2024

Related U.S. Application Data

(60) Division of application No. 16/384,166, filed on Apr. 15, 2019, now Pat. No. 11,844,954, which is a
(Continued)

(51) Int. Cl.
*A61N 1/39* (2006.01)

(52) U.S. Cl.
CPC ......... *A61N 1/3968* (2013.01); *A61N 1/3904* (2017.08); *A61N 1/3925* (2013.01); *A61N 1/3975* (2013.01)

(58) Field of Classification Search
CPC .. A61N 1/3968; A61N 1/3904; A61N 1/3825; A61N 1/3975
See application file for complete search history.

(56) References Cited

U.S. PATENT DOCUMENTS

| 3,724,355 A | 4/1973 | Busch et al. |
|---|---|---|
| 3,724,455 A | 4/1973 | Unger |

(Continued)

FOREIGN PATENT DOCUMENTS

| CN | 106374068 A | 2/2017 |
|---|---|---|
| DE | 2005060985 A2 | 6/2007 |

(Continued)

OTHER PUBLICATIONS

Stryker Sustainability Solutions, Protecting your patients; Web page (http://sustainability.stryker.com/products/safety-quality); 2017; 2 pages total.

(Continued)

*Primary Examiner* — Lynsey C Eiseman
*Assistant Examiner* — Amanda L Steinberg
(74) *Attorney, Agent, or Firm* — Polsinelli PC

(57) ABSTRACT

A wearable cardioverter defibrillator monitor case includes a housing configured to surround a defibrillator electronics assembly, a front cover removably attachable to the housing, and a rear cover removably attachable to the housing. The wearable cardioverter defibrillator case has a shock indicator positioned on the housing at an interface between the housing and the front cover.

18 Claims, 16 Drawing Sheets

Related U.S. Application Data continuation-in-part of application No. 29/669,668, filed on Nov. 9, 2018, now Pat. No. Des. 913,928, which is a continuation-in-part of application No. 16/186,368, filed on Nov. 9, 2018, now abandoned.

(60) Provisional application No. 62/662,107, filed on Apr. 24, 2018, provisional application No. 62/662,121, filed on Apr. 24, 2018, provisional application No. 62/662,114, filed on Apr. 24, 2018, provisional application No. 62/584,016, filed on Nov. 9, 2017.

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| D403,660 S | 1/1999 | Poon | |
| 5,902,249 A | 5/1999 | Lyster | |
| 5,913,685 A | 6/1999 | Hutchins | |
| 5,944,669 A | 8/1999 | Kaib | |
| 6,007,937 A | 12/1999 | Rodriguez et al. | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 6,980,419 B2 | 12/2005 | Smith et al. | |
| D517,987 S | 3/2006 | Castagnola et al. | |
| 7,065,401 B2 | 6/2006 | Worden | |
| 7,099,715 B2 | 8/2006 | Korzinov | |
| 7,212,850 B2 | 5/2007 | Prystowsky | |
| 7,559,902 B2 | 7/2009 | Ting et al. | |
| 7,587,237 B2 | 9/2009 | Korzinov | |
| 7,753,759 B2 | 7/2010 | Pintor et al. | |
| 7,865,238 B2 | 1/2011 | Brink | |
| 7,870,761 B2 | 1/2011 | Valentine et al. | |
| 7,880,591 B2 * | 2/2011 | Johnson | G06Q 20/40 |
| | | | 340/5.33 |
| 7,907,996 B2 | 3/2011 | Prystowsky | |
| 7,941,207 B2 | 5/2011 | Korzinov | |
| 7,974,689 B2 | 7/2011 | Volpe et al. | |
| D647,051 S | 10/2011 | Qualls et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,440,274 B2 | 5/2013 | Wang | |
| 8,527,028 B2 | 9/2013 | Kurzweil et al. | |
| D692,380 S | 10/2013 | Tirone | |
| 8,548,557 B2 | 10/2013 | Garstka et al. | |
| 8,560,044 B2 | 10/2013 | Kurzweil et al. | |
| D693,294 S | 11/2013 | Inskeep | |
| D695,681 S | 12/2013 | Nam et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,706,255 B2 | 4/2014 | Phillips et al. | |
| 8,742,349 B2 | 6/2014 | Urbon et al. | |
| 8,791,793 B2 | 7/2014 | Johnson | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| D742,307 S | 11/2015 | DeKeuster et al. | |
| 9,265,432 B2 | 2/2016 | Warren et al. | |
| D755,715 S | 5/2016 | Inskeep | |
| 9,345,898 B2 | 5/2016 | Piha et al. | |
| 9,408,548 B2 | 8/2016 | Volpe et al. | |
| 9,445,719 B2 | 9/2016 | Libbus et al. | |
| 9,454,219 B2 | 9/2016 | Volpe et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,724,008 B2 | 8/2017 | Sullivan et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| D870,042 S | 12/2019 | Chen | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2004/0143297 A1 | 7/2004 | Ramsey, III | |
| 2004/0179332 A1 | 9/2004 | Smith et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Vollpe et al. | |
| 2009/0005827 A1 | 1/2009 | Weintraub et al. | |
| 2009/0009945 A1 | 1/2009 | Johnson et al. | |
| 2010/0007413 A1 | 1/2010 | Herleikson et al. | |
| 2010/0298899 A1 | 11/2010 | Donnelly et al. | |
| 2010/0304091 A1 | 12/2010 | Wang | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0062916 A1 * | 3/2013 | Wiley | B60N 2/273 |
| | | | 116/203 |

(56) References Cited

U.S. PATENT DOCUMENTS

| | | | |
|---|---|---|---|
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0233235 A1* | 9/2013 | Wang | B32B 5/14 |
| | | | 116/200 |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0052135 A1 | 2/2014 | Aman et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0332417 A1 | 11/2014 | Wicks et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0256104 A1 | 9/2016 | Romem et al. | |
| 2016/0274162 A1 | 9/2016 | Freeman et al. | |
| 2016/0283900 A1 | 9/2016 | Johnson et al. | |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0162840 A1 | 6/2017 | Pendry | |
| 2017/0319862 A1 | 11/2017 | Foshee, Jr. et al. | |
| 2017/0367591 A1 | 12/2017 | Jorgenson | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |

FOREIGN PATENT DOCUMENTS

| | | | |
|---|---|---|---|
| EP | 2305110 A1 | 4/2011 | |
| JP | 2005507747 A | 3/2005 | |
| JP | 4320157 B2 | 8/2009 | |
| JP | 2014500099 A | 1/2014 | |
| JP | 2014526282 A | 10/2014 | |
| JP | 5963767 B2 | 8/2016 | |
| JP | 2017037845 A | 2/2017 | |
| RU | 2179769 C2 | 2/2002 | |
| WO | 1998039061 A2 | 9/1998 | |
| WO | 2011/146448 A1 | 11/2011 | |
| WO | 2012/064604 A1 | 5/2012 | |
| WO | 2012/151160 A1 | 11/2012 | |
| WO | 2015/056262 A1 | 4/2015 | |

OTHER PUBLICATIONS

Heartstart MRx and XL AED Algorithm—Application Note, Jul. 2011, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 20C0503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

WCD MONITOR SUPPORTING SERVICEABILITY AND REPROCESSING

CROSS-REFERENCE(S) TO RELATED APPLICATION(S)

This application is a divisional of U.S. patent application Ser. No. 16/384,166, filed Apr. 15, 2019, now issued as U.S. Pat. No. 11,844,954, which claims the benefit of U.S. Provisional Patent Application Nos. 62/662,114, filed Apr. 24, 2018, and claims the benefit of 62/662,121, filed Apr. 24, 2018, and claims the benefit of 62/662,107, filed Apr. 24, 2018, and is a continuation-in-part under 35 U.S.C. § 120 to U.S. Design patent application Ser. No. 29/669,668, filed Nov. 9, 2018, now issued as U.S. Design Patent No. D913928, issued on Mar. 23, 2021, which is a continuation-in-part of U.S. patent application Ser. No. 16/186,368, filed Nov. 9, 2018, which claims the benefit of U.S. Provisional Patent Application No. 62/584,016, filed Nov. 9, 2017, all of which are incorporated by reference herein in their entireties.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure is directed to wearable cardioverter defibrillator ("WCD") systems. WCD systems are used for patients who may be candidates for a future implantable defibrillator but do not currently meet the criteria for such a device. WCDs act as a bridge between an event such as a myocardial infarction or ex-plantation of an implantable cardioverter defibrillator ("ICD") and when the patient is a viable candidate for a new implant. WCD systems may monitor the patient's electrocardiography ("ECG") signals twenty-four hours a day, continuously processing them to determine if defibrillation therapy is needed.

WCD systems often include monitors that contain elements of the WCD system (e.g., electronics) and facilitate a patient's (or other user's) understanding of how the WCD system is operating. This patent discloses WCD monitors with features that allow for enhanced serviceability over the course of multiple patient usages.

WCD systems include one or more batteries, for example lithium ion batteries. When a patient is prescribed a WCD system, it may be desirable to ship the WCD system by air in order to minimize the time it takes to get the WCD system to the patient, who is at high risk of sudden cardiac death without it. However, lithium batteries are deemed to be dangerous goods, and transporting them by air is permitted with UN/DOT 38.3 certification according to the UN Manual of Tests and Criteria. These regulations permit shipping lithium batteries if they meet various limits for amounts of lithium content and watt-hour capacity that the design should meet, it also specifies that the batteries cannot be charged to more than 30% capacity.

To address the issue of shipping WCD batteries (as well as other issues), the present disclosure also provides battery conditioning devices for WCD systems. When preparing a WCD battery for air shipment, embodiments of the battery conditioning device will ensure that the battery capacity is less than a threshold, such as 30%. Embodiments may endeavor to ensure that the WCD system's battery is not discharged too much, because leaving the battery in a very low state of charge for too long may harm the battery. Embodiments of the battery conditioning device may charge or discharge until the capacity reaches some value below the threshold, and which provides adequate margin for capacity measurement accuracy. Embodiments of the battery conditioning device may include a housing with a docking station and contacts configured to electrically connect with contacts of a rechargeable battery to be conditioned.

The present disclosure also provides batteries for WCD systems, and in particular batteries having a mechanism configured to lock the battery to the WCD monitor, and to enable easy removal of the battery from the WCD monitor. Such batteries may be particularly suitable for use when the user suffers from arthritis, degraded vision, and/or reduced dexterity.

In an aspect, the present disclosure provides a wearable cardioverter defibrillator monitor case that includes a housing configured to surround a defibrillator electronics assembly, a front cover removably attachable to the housing, and a rear cover removably attachable to the housing. The wearable cardioverter defibrillator case includes a shock indicator positioned on the housing at an interface between the housing and the front cover. In some embodiments, the shock indicator is positioned within a recess. In some embodiments, the shock indicator is a mechanical or chemical shock indicator. In some embodiments, the front cover includes a window, which may be positioned on the front cover such that the shock indicator is visible when the front cover is removably attached to the housing. In some embodiments, the wearable cardioverter defibrillator monitor case may include a second shock indicator, and the shock indicator and the second shock indicator are positioned on different components of the wearable cardioverter defibrillator monitor case. In some embodiments, the housing has a battery opening configured to receive a cardioverter defibrillator battery. In some embodiments, the front cover is sized to substantially cover a front face of the housing when removably attached to the housing. In some embodiments, the rear cover is sized to substantially cover a rear face of the housing when removably attached to the housing. In some embodiments, the front cover or the rear cover is configured to conceal a plurality of attachment devices that attach the defibrillator electronics assembly to the housing. In some embodiments, the front cover and the rear cover are independently detachable from the housing. In some embodiments, the case is configured to be detached from the cardioverter defibrillator electronics assembly by removal of a plurality of attachment devices. In some embodiments, the front cover is configured to conceal the shock indicator from view when the front cover is removably attached to the housing.

In another aspect, the present disclosure provides a wearable cardioverter defibrillator monitor having a monitor case, a cardioverter defibrillator electronic assembly positioned inside the monitor case, and a battery that is removably receivable within the monitor case. The monitor case includes a housing configured to surround the cardioverter defibrillator electronics assembly, a front cover removably attachable to the housing, a rear cover removably attachable to the housing, and a shock indicator positioned on the case at an interface between the housing and the front cover.

In another aspect, the present disclosure provides a method of servicing a wearable cardioverter defibrillator monitor case. The method includes receiving a wearable cardioverter defibrillator monitor case from a first user, the wearable cardioverter defibrillator monitor case having a housing configured to surround a defibrillator electronics assembly, a front cover removably attachable to the housing, a rear cover removably attachable to the housing, and a shock indicator positioned on the case at an interface between the housing and the front cover. The method also includes removing the front cover from the housing and attaching a replacement front cover to the housing. In some embodiments, the method includes inspecting the shock indicator for a sign of a shock in excess of a shock threshold. In some embodiments, the method includes replacing the shock indicator. In some embodiments, the method includes removing the rear cover from the housing and attaching a replacement rear cover to the housing. In some embodiments, the method includes removing a defibrillator electronics assembly from the housing and functionally testing the defibrillator electronics assembly. In some embodiments, the method includes sending the wearable cardioverter defibrillator case to a second user, the first user being different from the second user.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
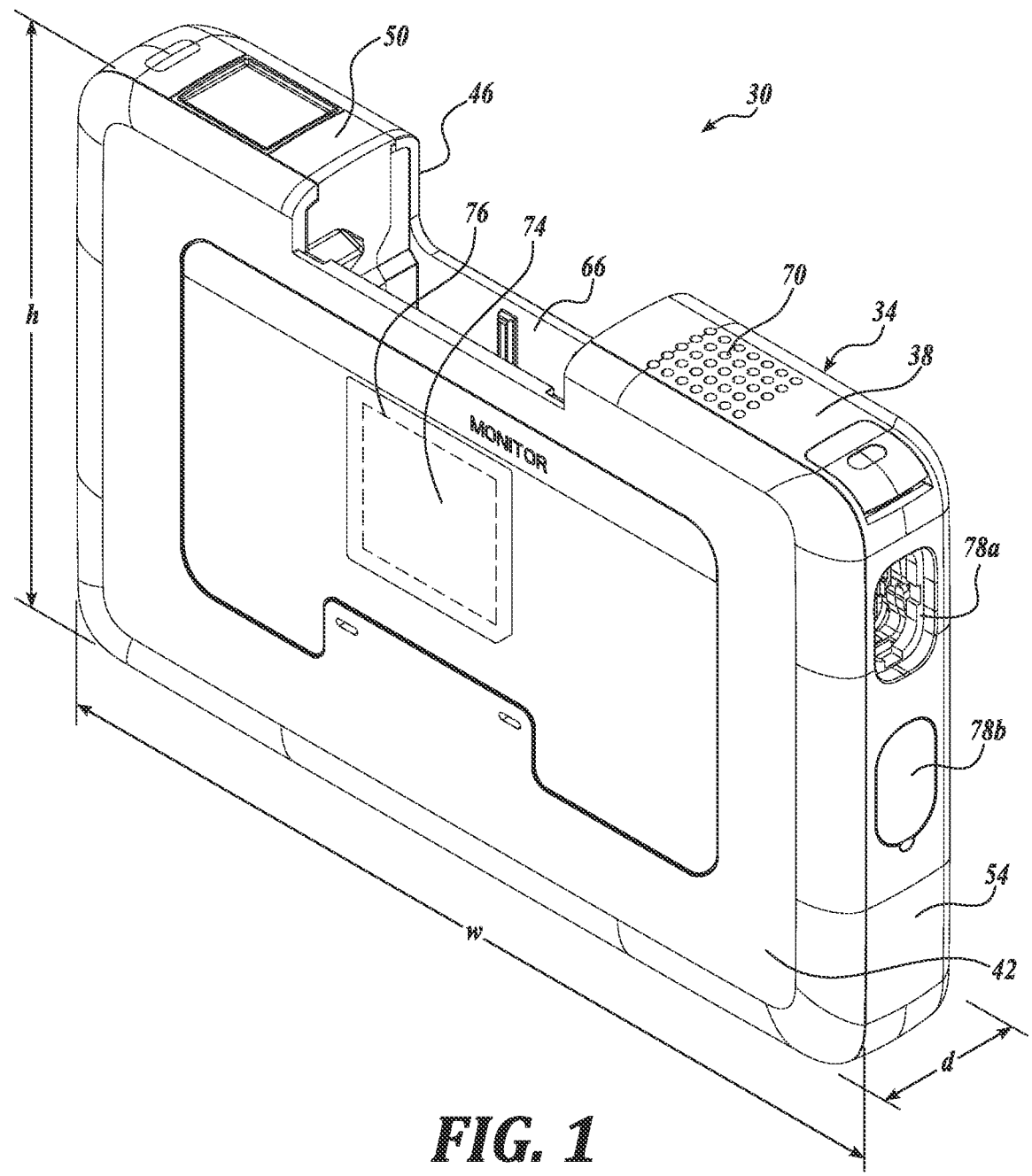
FIG. 1 is an upper front perspective view of a WCD monitor according to the present disclosure.
Figure 2:
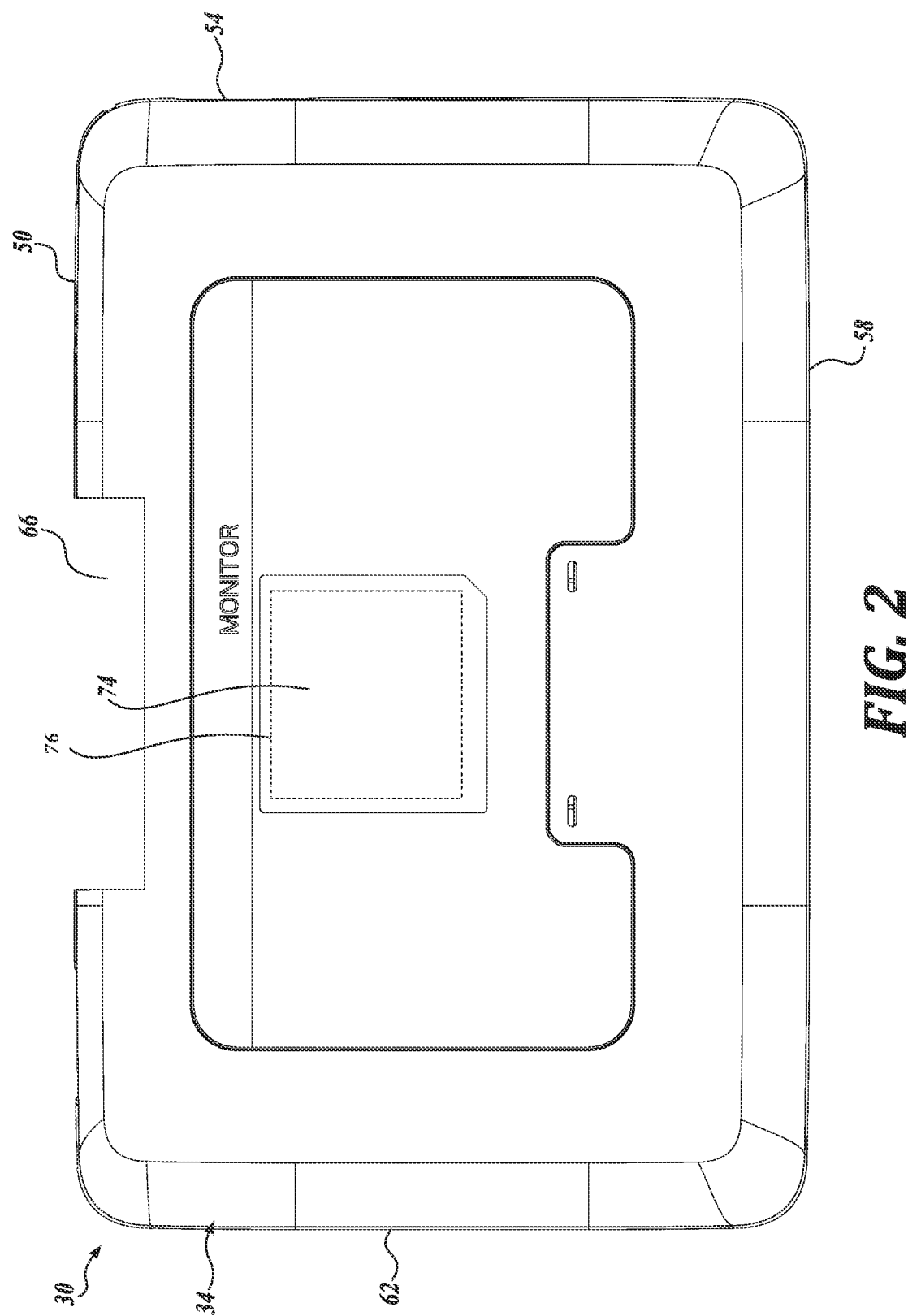
FIG. 2 is a front view of the WCD monitor of FIG. 1.
Figure 3:
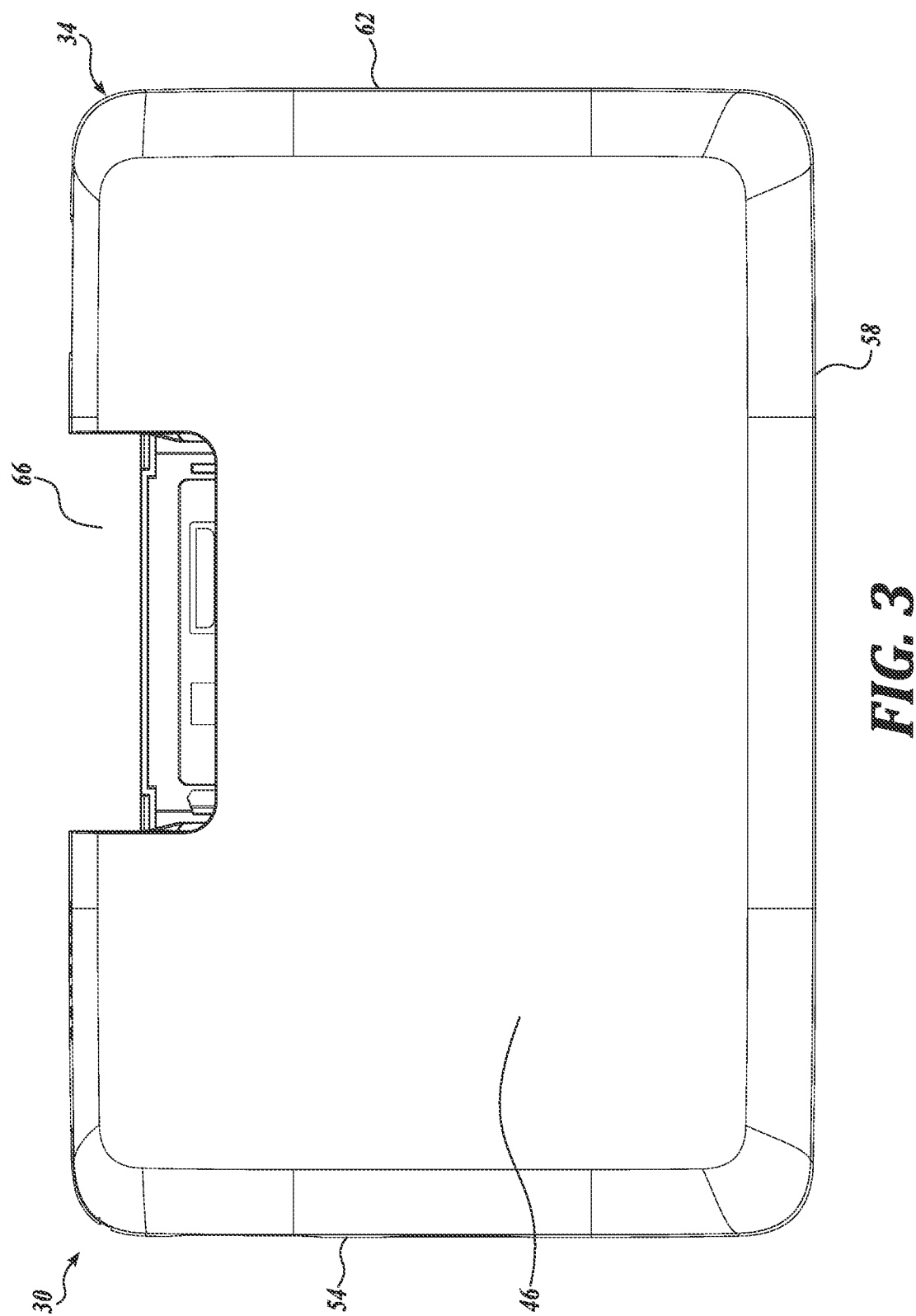
FIG. 3 is a rear view of the WCD monitor of FIG. 1.
Figure 4:
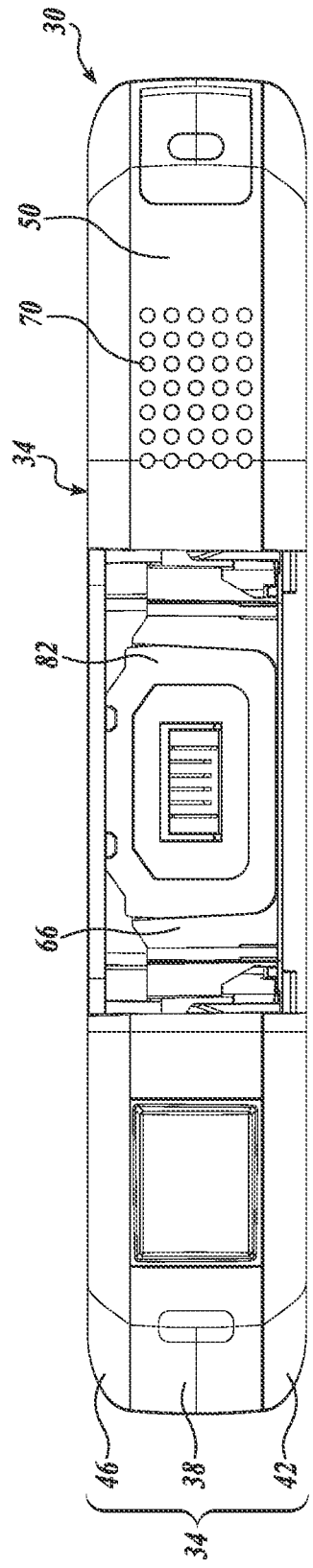
FIG. 4 is a top view of the WCD monitor of FIG. 1.
Figure 5:
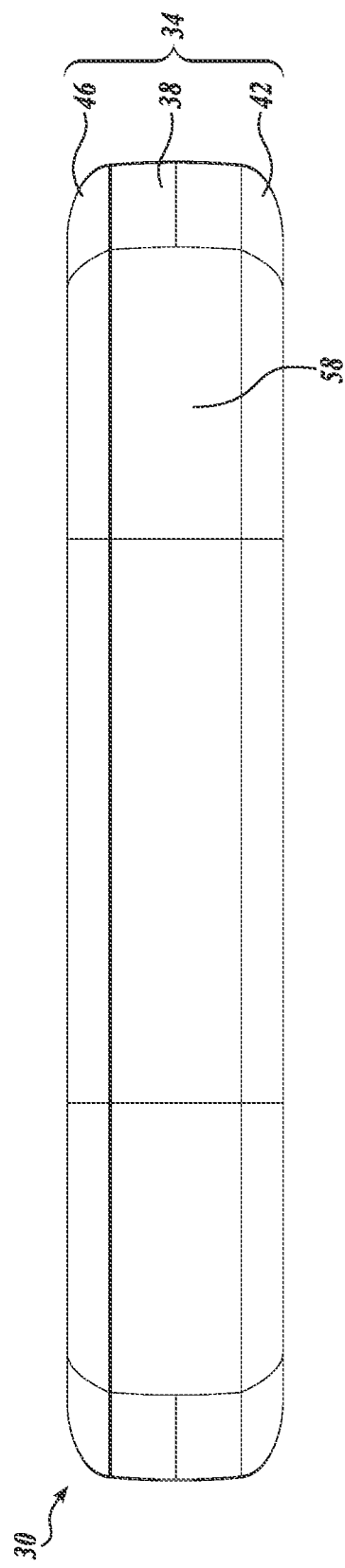
FIG. 5 is a bottom view of the WCD monitor of FIG. 1.
Figure 6:
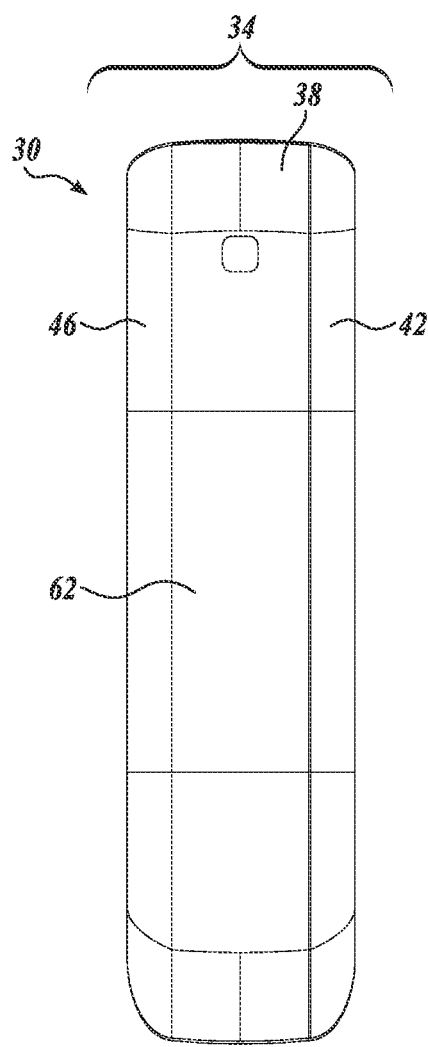
FIG. 6 is a left view of the WCD monitor of FIG. 1.
Figure 7:
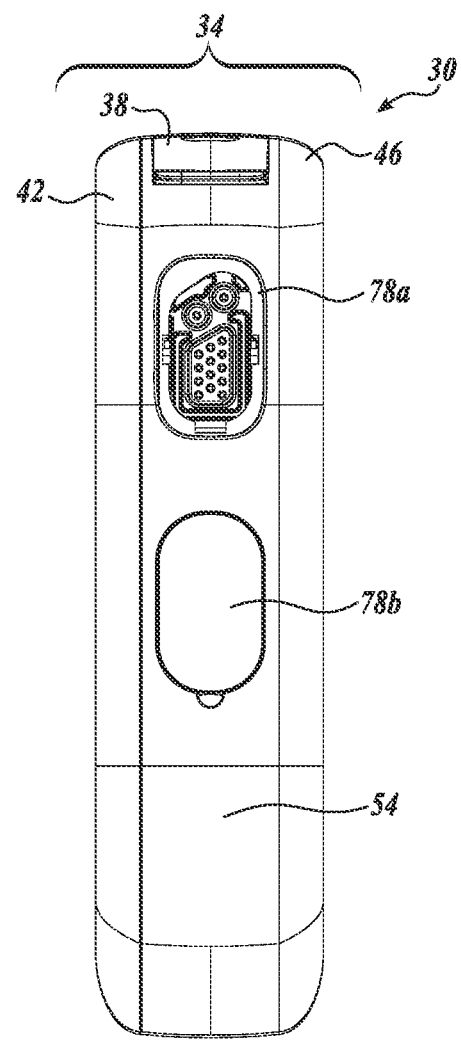
FIG. 7 is a right view of the WCD monitor of FIG. 1.
Figure 8:
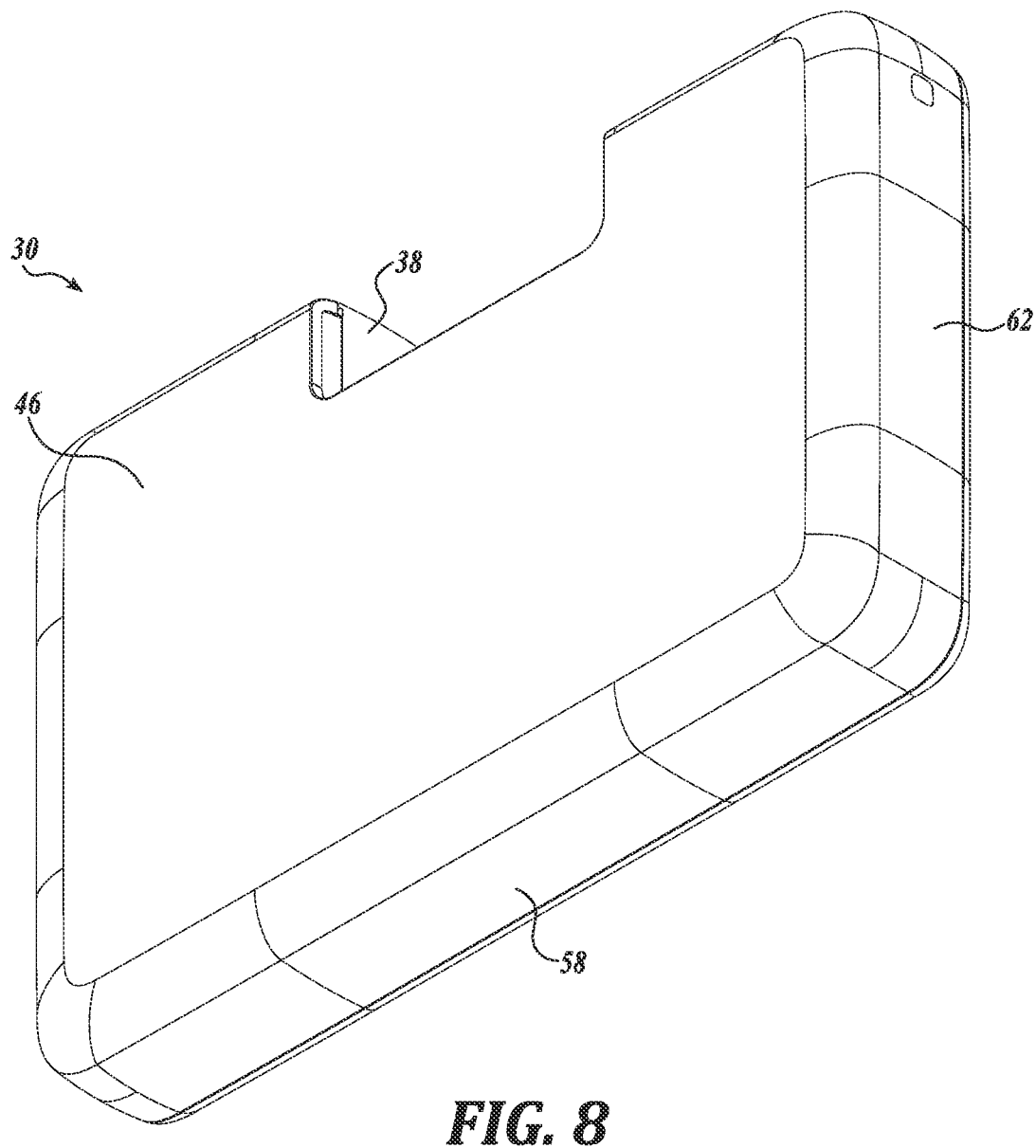
FIG. 8 is a lower rear perspective view of the WCD monitor of FIG. 1.
Figure 9:
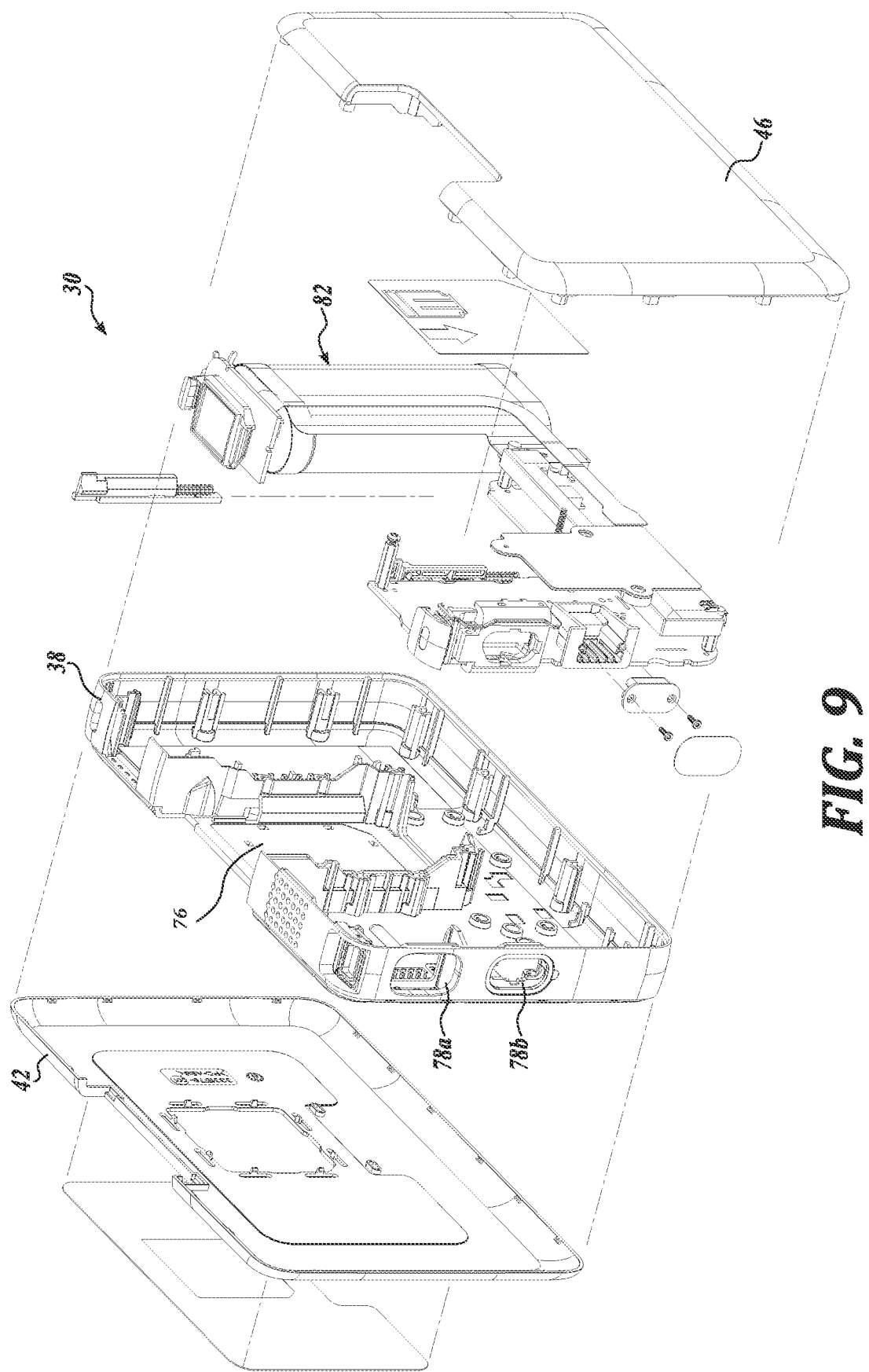
FIG. 9 is an exploded view of the WCD monitor of FIG. 1.
Figure 10:
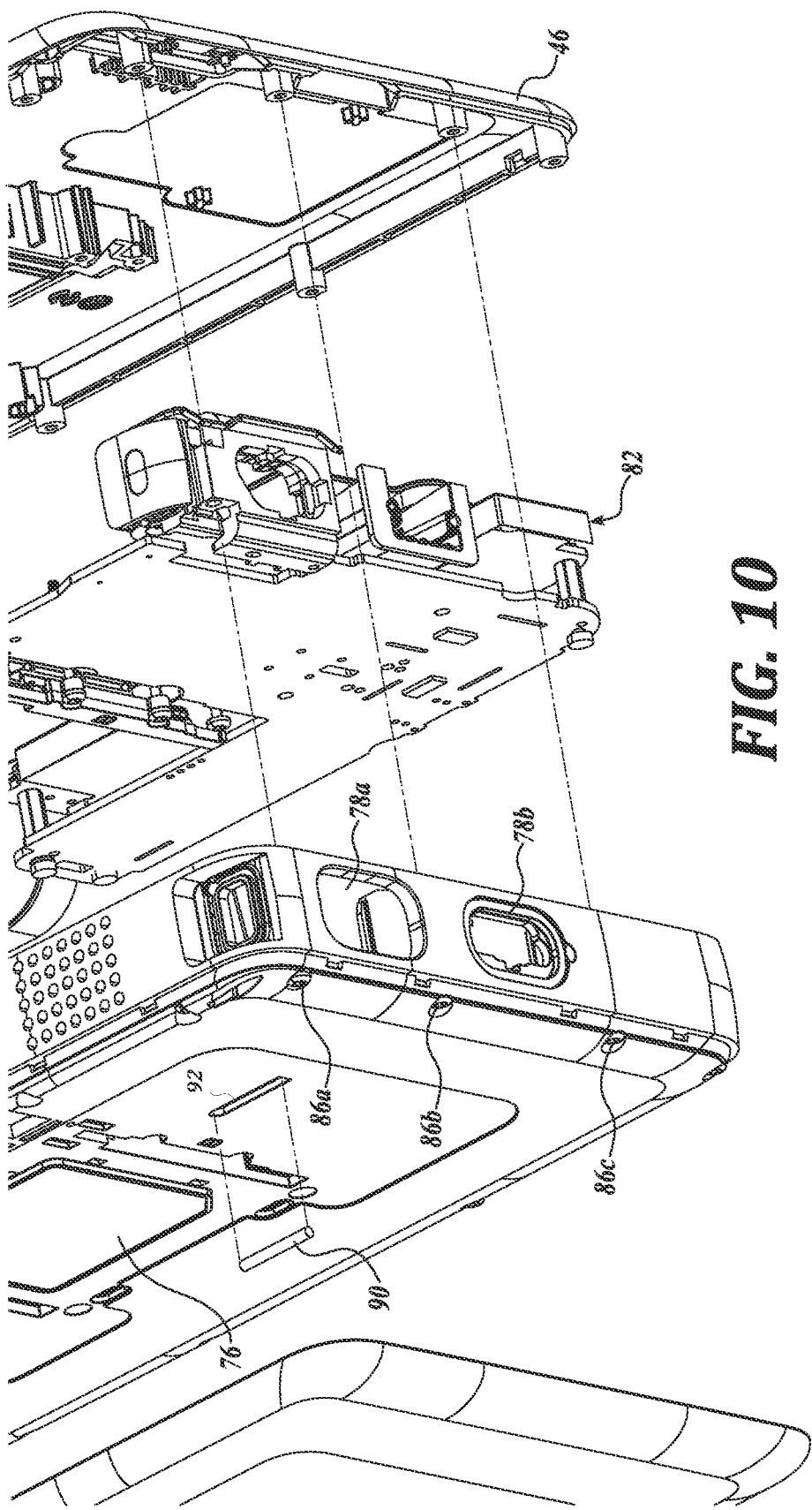
FIG. 10 is a partial exploded view of the WCD monitor of FIG. 1.

Referring to FIGS. 1-8, a wearable cardioverter defibrillator ("WCD") monitor 30 includes an enclosure assembly 34 that is configured to protect defibrillator electronics contained therein (electronics are shown in FIGS. 9-10, described below). The enclosure assembly 34 is generally a multi-piece assembly that includes a housing 38, a front cover 42, and a rear cover 46. The housing 38 generally lies in between the front cover 42 and the rear cover 38. The housing 38, the front cover 42, and the rear cover 46 may each be constructed from one or more durable materials capable of withstanding shocks, abrasions, and other forces likely to be encountered when the WCD monitor 30 is worn by a patient. In the non-limiting embodiment of FIGS. 1-8, the enclosure assembly 34 is primarily constructed of one or more plastics, for example acrylonitrile butadiene styrene and/or polycarbonate. In an embodiment, the enclosure assembly 34 may be constructed of one or more metals, e.g., aluminum. In some embodiments, the front cover 42 may be patient-facing, i.e., closest to the patient. In some embodiments, the rear cover 46 may be patient facing, i.e., closest to the patient. Accordingly, the use of "front," "rear," "left," "right," "top," and "bottom," is intended to facilitate understanding and is not intended to limit the orientation of the WCD monitor 30 in use with respect to the patient.

The enclosure assembly 34 may have a size that varies between embodiments, but may generally be sized to enable easy carrying by a human patient. For example, the patient may carry the WCD monitor 30 on a belt, in a purse, in a backpack, in a pocket, in-hand, etc. The enclosure assembly 34 of FIGS. 1-8 has a width, w, a depth, d, and a height, h. The dimensions and shapes of the enclosure assembly 34 may vary between embodiments. For example, the enclosure assembly 34 of FIGS. 1-8 is generally rectangular; the housing 38 has a top wall 50, a right wall 54, a bottom wall 58, and a left wall 62. Other embodiments may have a different shape, e.g., triangular, square, circular, a non-polygonal shape, etc.

Figure 12:
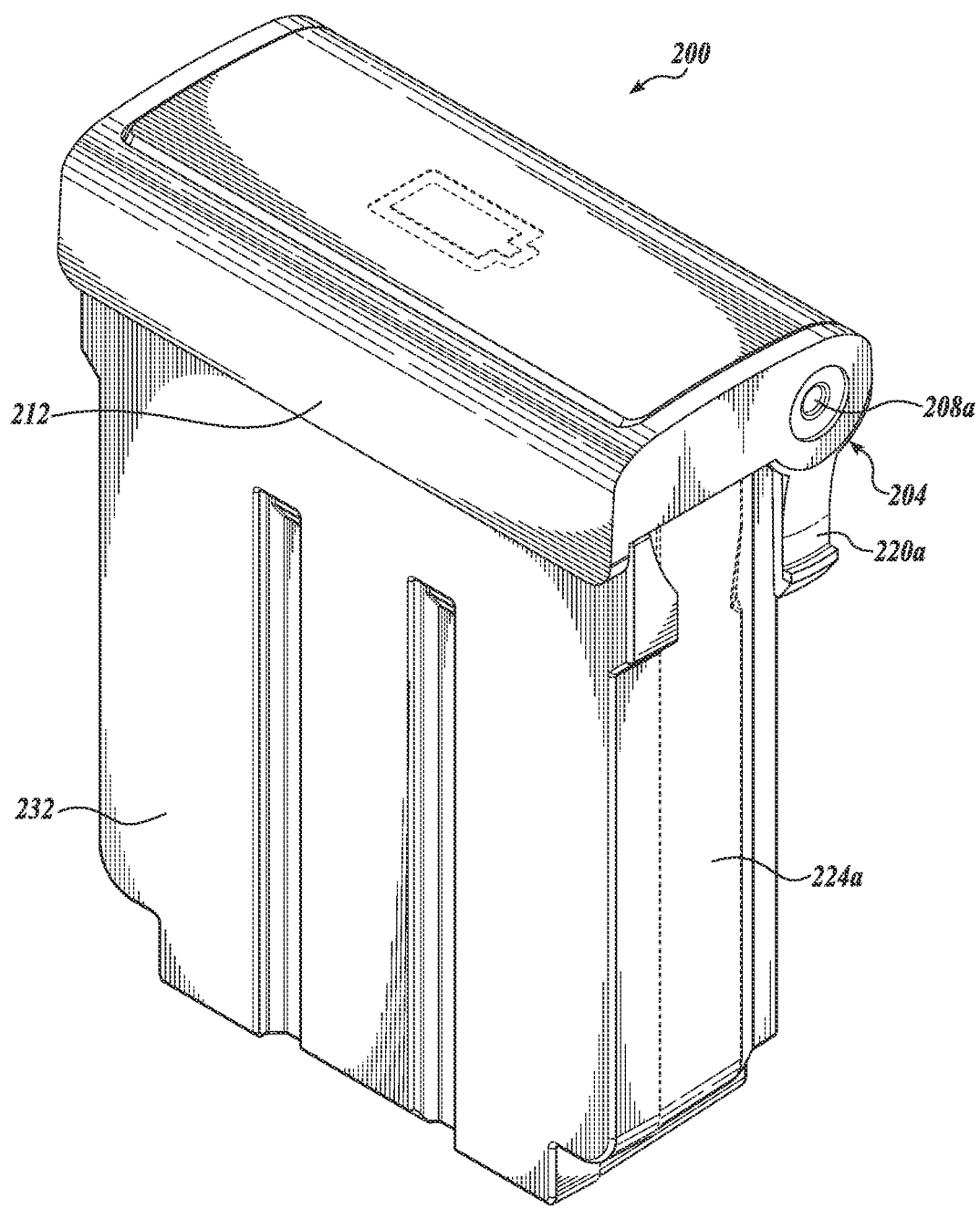
FIG. 12 is a perspective view of a removable battery for the WCD monitor of FIG. 1, shown with a handle in a closed position.
Figure 13:
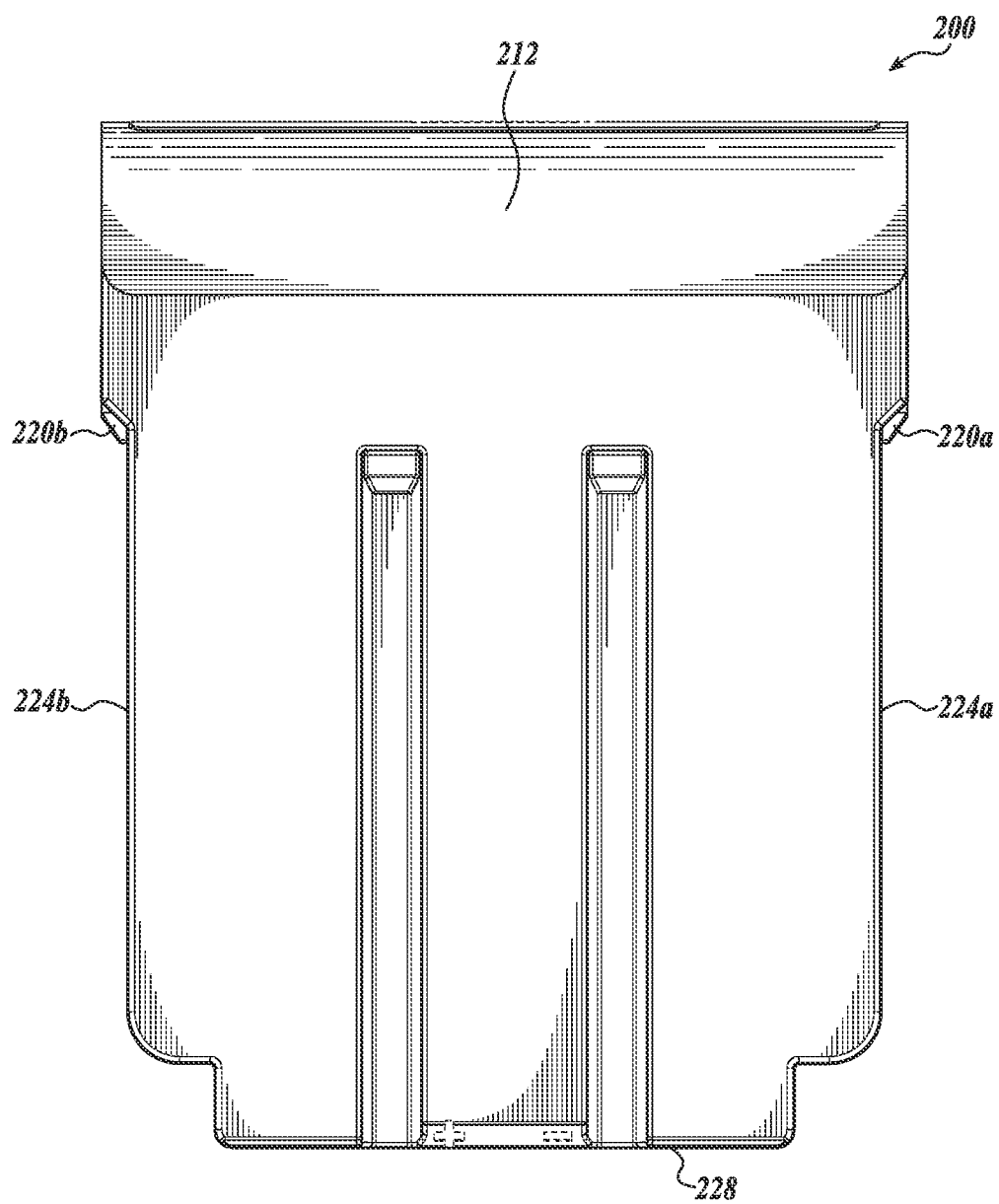
FIG. 13 is a front view of the removable battery shown in FIG. 12.
Figure 14:
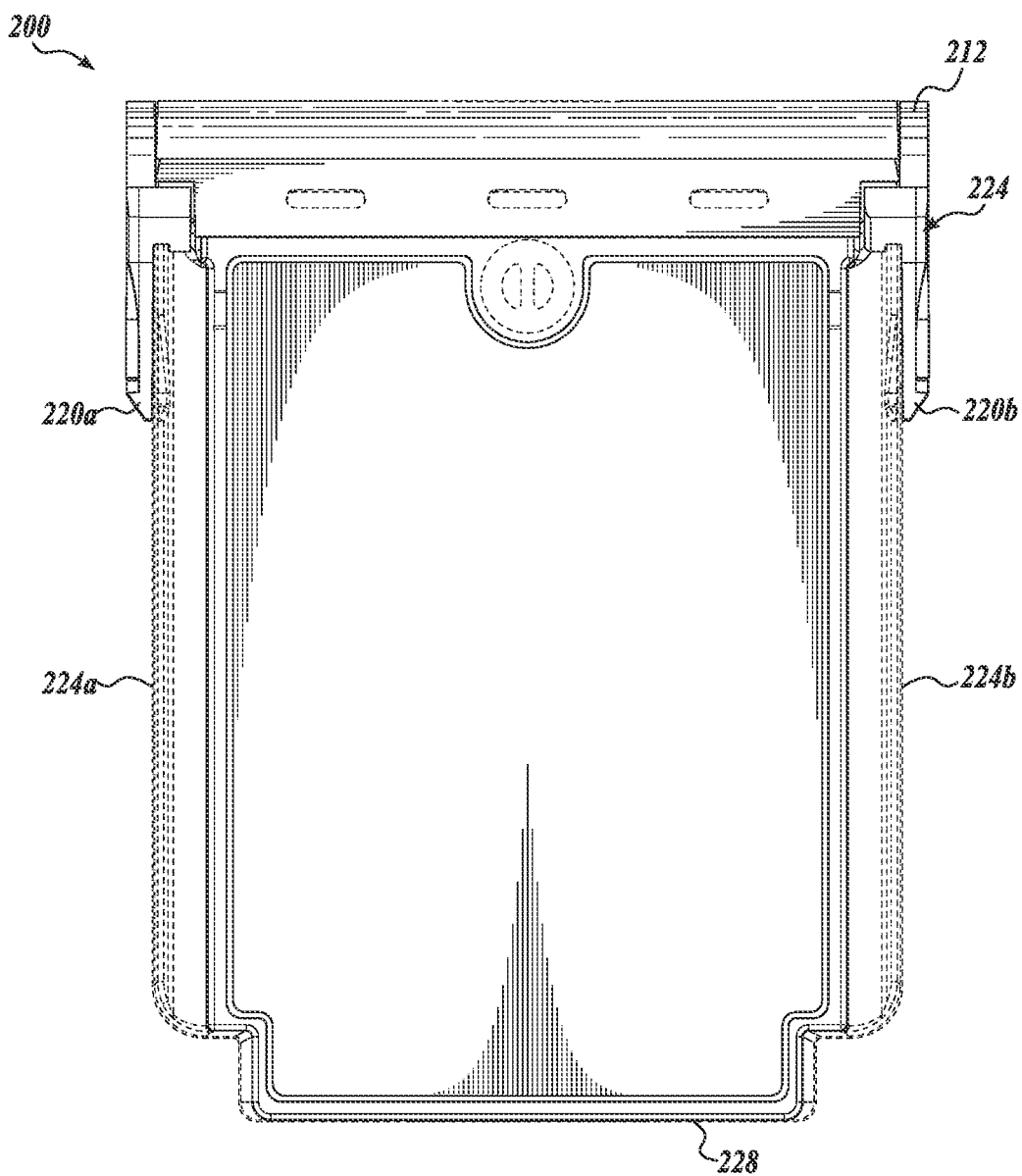
FIG. 14 is a rear view of the removable battery shown in FIG. 12.
Figure 15:
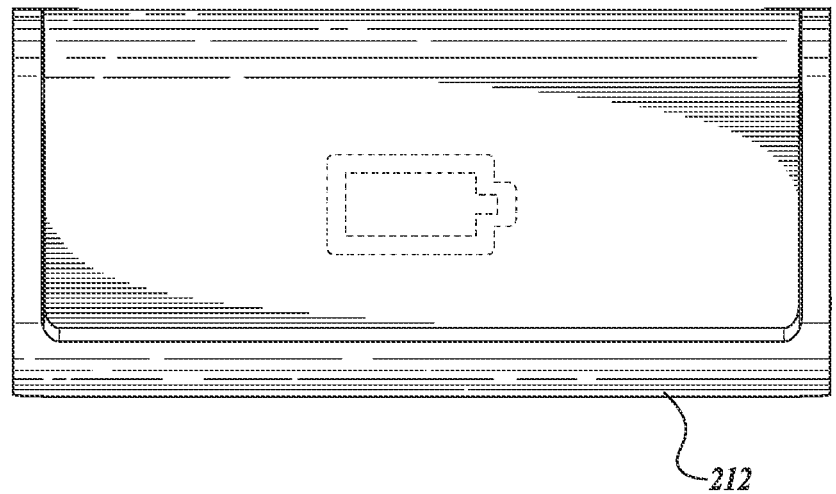
FIG. 15 is a top view of the removable battery shown in FIG. 12.
Figure 16:
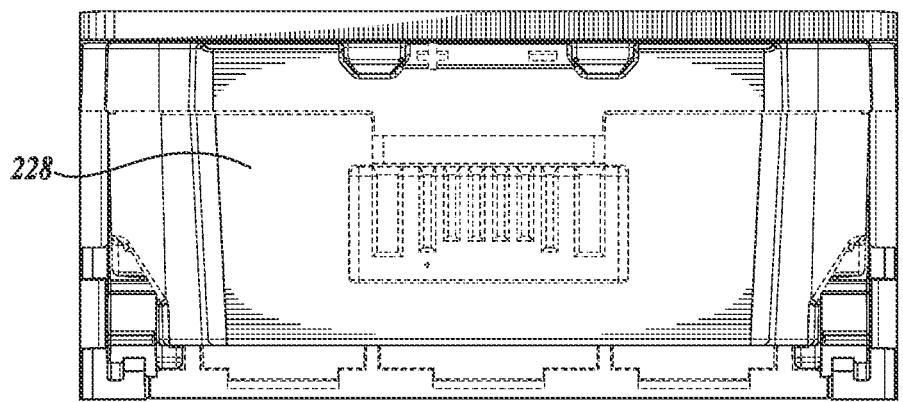
FIG. 16 is a bottom view of the removable battery shown in FIG. 12.
Figure 17:
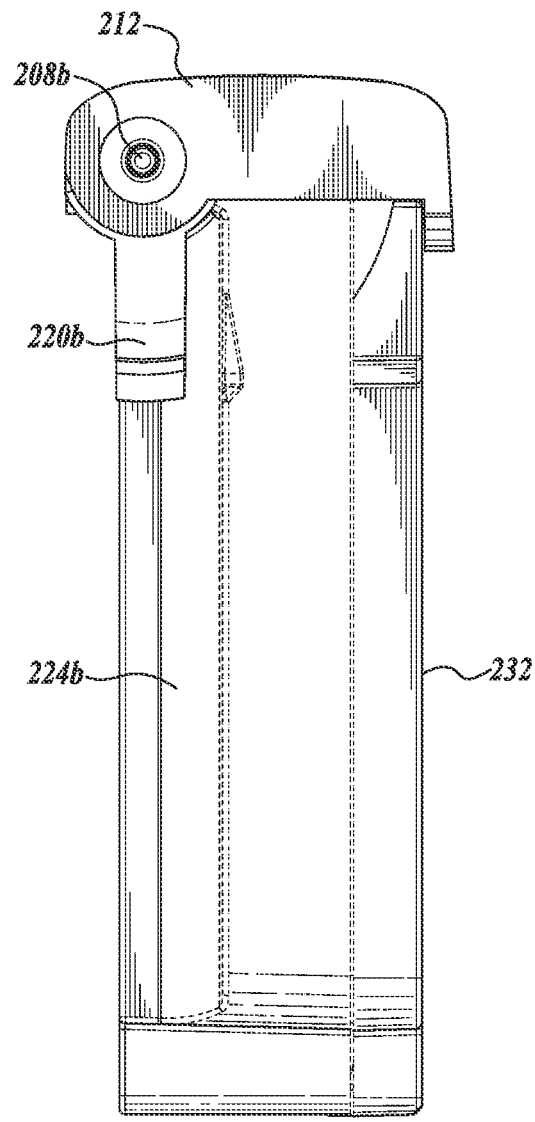
FIG. 17 is a left side view of the removable battery shown in FIG. 12.
Figure 18:
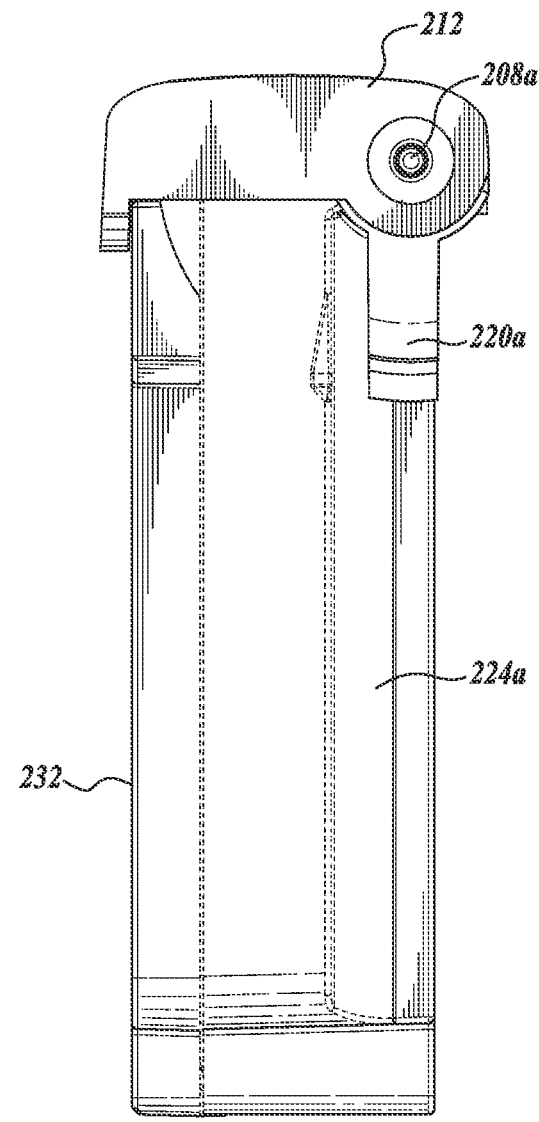
FIG. 18 is a right side view of the removable battery shown in FIG. 12.
Figure 19:
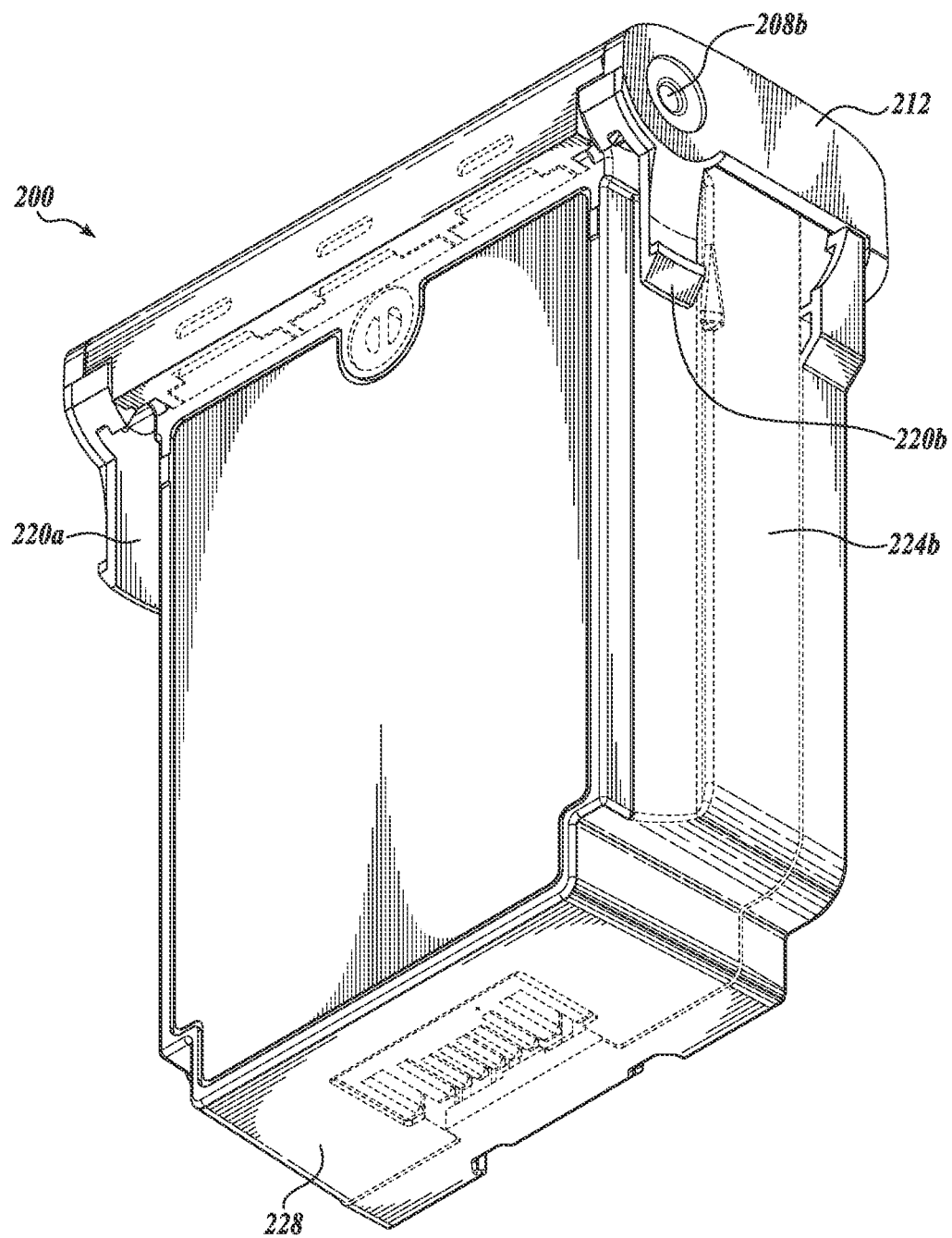
FIG. 19 is a second perspective view of the removable battery shown in FIG. 12.

The enclosure assembly 34 may include a battery opening 66 that is sized and located to enable insertion and removal of a battery (such as the battery 200 of FIG. 12). The enclosure assembly 34 may also include one or more additional features, including: an audio outlet 70 to enable a user to hear audible signals broadcast from within the housing 38; a window 74 through which a user can view a display 76; one or more ports 78a, 78b through which a user may plug a power cord, a data cord, or another cord into the WCD monitor 30; and branding, labels, indicia, ornamentation, etc. Any one or combination of the foregoing features may exist on any aspect of the enclosure assembly 34. In the embodiment of FIGS. 1-8, the battery opening 66 and audio outlet 70 are located in the top wall 50 of the housing 38; similarly, the right wall 54 includes two connector ports 78a, 78b. The front cover 42 may include a window 74, through which the display 76 is visible. The locations of the features shown in the embodiment of FIGS. 1-8 may vary in other embodiments.

Referring now to the exploded view of FIG. 9, the enclosure assembly 34 is configured to protect defibrillator electronics, including interconnected circuit cards, flex circuits, cables, a high voltage capacitor, antennas, connectors, a speaker, a display, a battery (e.g., a lithium battery), a user input device (e.g., a touch screen and/or buttons). To facilitate service or interchangeability with other WCD units, some or all of the defibrillator electronics may be packaged in a modular board stack 82, on which a substantial number of the electronic components can be decoupled from the enclosure assembly 34 without disassembly of the electronic interconnections.

The housing 38 has a size and shape that is configured to surround the board stack 82, e.g., surround at least an outer edge of the board stack 82. In an embodiment, the housing 38 is configured to at least partially cover a front and/or a rear side of the board stack 82. In such embodiments, the front cover 42 is configured to interface with, and removably attach to, a front side of the housing 38; likewise, the rear cover 46 is configured to interface with, and removably attach to, a rear side of the housing 38.

It may be desirable that the electronics contained within the enclosure assembly 34 are not easily accessed, to prevent inadvertent tampering and damage by patients who are physically away from supervision of healthcare professionals. Referring also to FIG. 10, the board stack 82 is removably retained in the housing 38 via a plurality of attachment devices 86 (in this embodiment, screws 86), which are positioned around a perimeter of the housing 38. Other attachment devices (e.g., snaps, adhesive, etc.) may be used to attach the board stack 82 to the housing 38, and at different locations. In normal use, the housing 38 and rear cover 46 conceal the board stack 82, and the front cover 42 conceals the screws 86 from view.

While the WCD monitor 30 is designed for use during multiple prescriptions, it is likely that the enclosure assembly 34 may become scuffed, scraped, dinged, and otherwise damaged. Because the board stack 82 and other electronics contained therein may be in excellent working condition, it may be desirable to periodically replace or refurbish one or more components of the enclosure assembly 34, such as when the front cover 42 and/or rear cover 46 is damaged or has a degraded appearance.

Referring again to FIG. 9, the enclosure assembly 34 is specifically designed to be separable from the electronics 82 within, for example to facilitate replacement of the one or more components of the enclosure assembly 34, the board stack 82, etc. To this end, the front cover 42 and the rear cover 46 of the enclosure assembly 34 are each removably attachable to the housing 38 to enable quick removal of the front and rear covers 42, 46 from the housing 38. In some embodiments, the front and rear covers 42, 46 may be removably attachable to the housing 38 by other retention means, including screws, magnets, and/or adhesive. In an embodiment, the front cover 42 or rear cover 46 may be removable from the housing 38, while the other cover (i.e., the rear cover 46 or the front cover 42) may be fixed to the housing 38 or integrally formed with the housing 38. In an embodiment, the front cover 42 and rear cover 46 may each be integrally formed with the housing 38, and the housing 38 itself may be a separable assembly that includes more than one piece.

The WCD monitor 30 (or portions thereof) may be reused through more than one prescription, reprocessing, and refurbishment. Because the WCD monitor 30 is designed for use away from the supervision of a healthcare professional, it may be difficult to for a distributor, servicer, or manufacturer to assess the extent to which the WCD monitor 30 experienced abuse during a previous prescription. While functional testing during reprocessing may help rule out functional issues, latent defects resulting from prior abuse may not be revealed by functional testing.

Referring again to FIG. 10, the WCD monitor 30 includes a shock indicator 90 that is positioned in a recess 92 on the housing 38. The shock indicator 90 produces a detectable change or signal if the WCD monitor 30 has experienced a significant mechanical shock, i.e., a shock that is sufficient to cause damage or otherwise compromise future performance—in particular performance of the electronic components. In a current embodiment, the shock indicator 90 provides a visual and/or audible signal in response to a force and/or an acceleration that exceeds a predetermined shock threshold. Exemplary shock thresholds may range from about 1 G to about 100 G, e.g., about 1 G, 2G, 3G, 4G, 5G, 10 G, 25 G, or any other value in that range. For example, the shock indicator 90 may include a translucent or transparent window, button, or tube (e.g., a vial containing fluid) that changes color from a first color to a second color after experiencing a shock load that exceeds a threshold (e.g., 10 G). The shock indicator 90 may be replaceable, and may be a mechanical shock indicator (e.g., a spring device), a chemical shock indicator (a liquid-vial type indicator), or an electronic shock indicator (e.g., a shock indicator having one or more accelerometers, gyroscopes, or other electronic sensors). Because mechanical and chemical shock indicators may detect shocks without reliance on a battery or other power source, such shock indicators may advantageously perform even when a WCD monitor is powered down and/or when a WCD battery is depleted. As an additional advantage, the shock indicator 90 may provide valuable information on the health of the WCD monitor 30 without powering up or opening the unit. Additionally or alternatively to a visual or audible signal, the shock indicator 90 may transmit a communications signal (e.g., cellular, RFID, WI-FI®, BLUETOOTH®, ZIGBEE®, or other signal) after experiencing a shock load that exceeds a threshold. In such embodiments, the WCD monitor 30 may optionally include a transponder or transceiver (not shown) for broadcasting such a signal. The WCD monitor 30 may comprise part of a WCD system that includes a receiver for receiving such a signal, which receiver may be remote from the WCD monitor 30 itself (e.g., a remote monitoring receiver operated by the WCD monitor manufacturer or distributor).

In the embodiment of FIGS. 1-10, the shock indicator 90 is not visible or accessible without removing the front cover 42, to reduce the likelihood that a user will reset or replace the shock indicator 90. In other embodiments, the shock indicator 90 is configured to record any detected shocks on a memory device (not shown) located in the board stack 82.

By placing the shock indicator 90 on the WCD monitor 30 (e.g., on the enclosure assembly 34), it is possible to determine during reprocessing or service if there may be reason to fully open the WCD monitor 30 and search for additional evidence of damage. In some embodiments, it may be advantageous to utilize more than one shock indicator 90, e.g., a first shock indicator 90 positioned on the enclosure assembly 34 and a second shock indicator positioned on the board stack 82. The shock indicator 90 may be located on the WCD monitor 30 at a particular location that increases the relevance of its indication. For example, the shock indicator 90 may be positioned on the enclosure assembly 34 at or near a corner, an edge, or a face that is more likely to experience a damaging shock. For example, the front cover 42 may be particularly likely to experience a shock when a patient wears the WCD monitor 30 on a belt, and therefore the shock indicator 90 may be positioned either on the front cover 42 or on the housing 38 adjacent the front cover 42. As another example, the rear cover 46 may be likely to experience a shock when a patient sets the WCD monitor down on a surface (e.g., a table); therefore the shock indicator 90 may be positioned either on the rear cover 46 or on the housing 38 adjacent the rear cover 46. Similarly, one of the lower corners of the WCD monitor 30 may be more likely to contact the ground than the upper corners; therefore, the shock indicator 90 may be positioned on the housing 38 near one of the lower corners. These locations are merely exemplary, and the placement of one or more shock indicators may vary between embodiments.

In the embodiment of FIG. 10, the shock indicator 90 is located on the housing 38, as opposed to the front cover 42 or rear cover 46. The housing 38 is nearer to the board stack 82 in this configuration, and therefore it is more likely to experience shock loads that approximate shock loads experienced by the board stack 82 contained therein. This positioning of the shock indicator may reduce false positive alerts. In another embodiment, the WCD monitor 30 may include a first shock indicator 90 that is located on the housing 38 and a second shock indicator that is located on the board stack 82. Another embodiment may include additional shock indicators, for example a third shock indicator that is located on the front cover 42 (such as behind a window) to enable inspection without removing any parts.

In use, a user (e.g., a manufacturer, distributor, servicer, etc.) may obtain a WCD monitor 30. For example, a distributor may receive a WCD monitor 30 from a user who recently received an ICD device. After receipt, the user may optionally inspect the WCD monitor 30 for signs of damage e.g., by inspecting the enclosure assembly 34, including the housing 38 and the front and rear covers 42, 46. The inspection may include a visual inspection for scratches, cracks, missing parts, etc. The inspection may additionally or alternatively include functional testing, for example functional testing of the board stack 82 for proper defibrillator performance.

In the embodiment shown in FIG. 9, the front cover 42 is removed to view the shock indicator 90. For example, the user's health care provider may remove the front cover 42 during office visits to determine if a potentially damaging shock has occurred, and if the WCD monitor 30 should be replaced or further inspected. Subsequent to the optional inspection, the user may completely or partially disassemble the WCD monitor 30. For example, the user may remove the front cover 42 and/or the rear cover 46 from the housing 38. To remove the front and/or the rear cover (42, 46), the user may unsnap, unscrew, or otherwise detach the front and/or rear cover 42, 46 from the housing 38.

If the WCD monitor 30 is equipped with additional shock indicators 90 as described above, the user may inspect such shock indicator(s) 90 for evidence of a potentially damaging shock. If the shock indicator 90 shows that the WCD monitor 30 has experienced a potentially damaging shock, the user may replace one or more of the components, for example the front cover 42, the rear cover 46, the housing 38, the shock indicator 90, and/or the board stack 82. The user may additionally or alternatively subject the WCD monitor 30 to further functional testing. The user may send the WCD monitor 30 back to the original user or to a different user.

Figure 11:
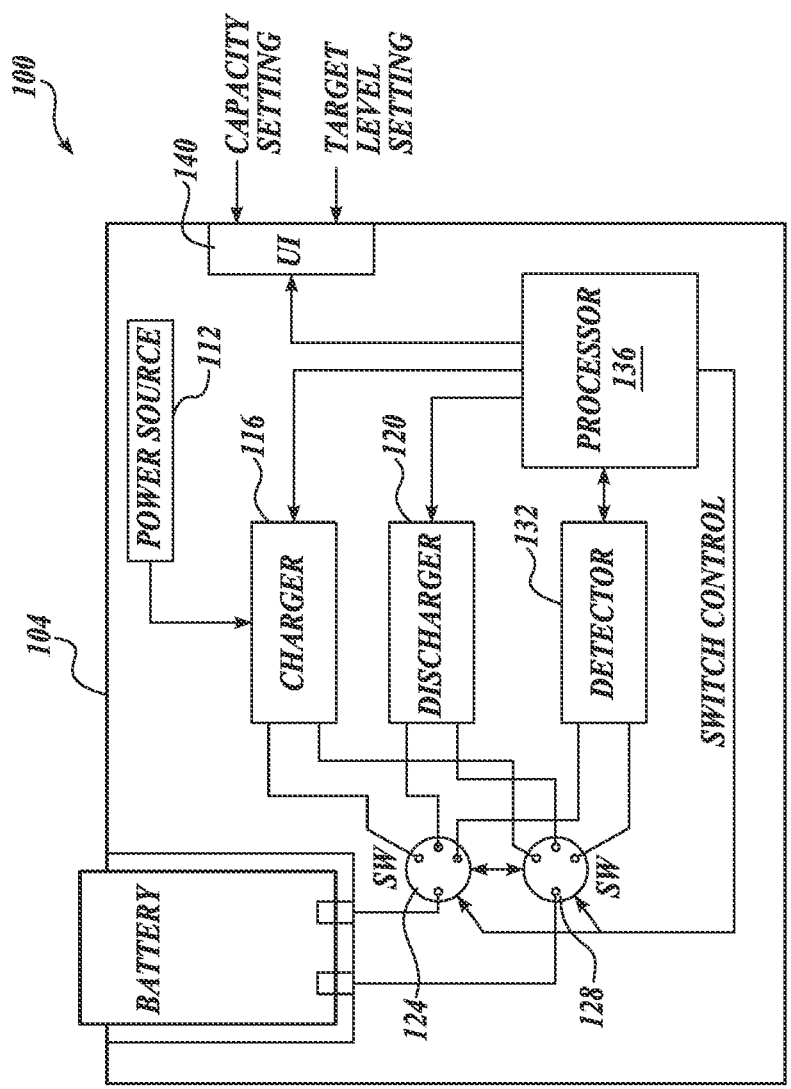
FIG. 11 is a schematic of a battery conditioning system of the present disclosure.

WCD monitors 30 of the present disclosure may include an optional battery conditioning system. FIG. 11 schematically illustrates such a battery conditioning system 100, which includes a housing 104 configured to receive a rechargeable battery 108. In some embodiments, the housing 104 may be a docking station. The docking station is optional, however, as a lack of a docking station facilitates conditioning of rechargeable batteries of different shapes, of different capacities, etc. The battery conditioning system 100 generally utilizes a power source 112, such as a charging battery or line power from an electrical outlet. In an embodiment, the battery conditioning system 100 may be implemented as a subsystem in a WCD monitor such as WCD monitor 30 described above with respect to FIG. 1-10. In an embodiment, the battery conditioning system 100 may be embodied on storage media which, when performed by a processor of a WCD monitor 30 as described herein, results in the actions/operations described below.

The battery conditioning system 100 may include a charger 116 and a discharger 120, which may be alternately connectable to the battery 108 via switches 124, 128. Some embodiments of battery conditioning system 100 may sense the present charge of the battery 108 by a detector 132, which can sense the battery charge as a fraction of the whole capacity, for example.

The detector 132 may be separately connectable to the rechargeable battery 108, for example via the switches 124, 128, or sense unobtrusively the voltage or current of the battery 108 without a separate setting of the switches 124, 128. For example, the voltage of the battery 108 may be sensed across via a high-impedance connection, etc.

A processor 136 can control the switches 124, 128 via a signal. The processor 136 can be digital or analog. For example, an analog processor 136 may be preferable when the logic is relatively simple and the functions of the processor 136 can be implemented together with the detector 132.

A user interface 140 on the battery conditioning system 100 can receive inputs, e.g., a target charge capacity setting, a maximum charge threshold, and/or a minimum charge threshold. The logic can be implemented in a number of ways. For example, some embodiments may charge the battery 108 to the full capacity, and then discharge enough to get the battery 108 below the target threshold. Some embodiments may discharge the battery 108 completely, and then charge the battery 108 enough but not enough to get the battery 108 over the target threshold. Charging and/or discharging can be done while detecting electrical parameters.

Discharging can be accomplished simply by using one or more of the switches 124, 128 to apply a load resistor to the battery output. The load resistor will turn the battery energy into heat, which will be safely managed by the housing 104 design. Tradeoffs between discharge rate, max temperature and load resistor and enclosure assembly size may be necessary. In such embodiments, such a resistor may be located within the housing 104.

In an embodiment, the battery conditioning system 100 may include any one or more of the following features: an LCD display on the housing 100 to present information about the rechargeable battery 108 and charge status; a remote interface to a computer for automatically performing testing and logging the results to a database; the ability to electrically connect to one or more other charger/dischargers so that a plurality of batteries may be conditioned simultaneously and managed/controlled by one computer (for example, as one rechargeable battery 108a is being discharged because its charge level exceeds a threshold, that charge could be used to charge another rechargeable battery 108b whose charge level is below the threshold); the ability to test functions of the rechargeable battery 108 by communicating with it and reading status and error logs; the ability to determine the series impedance of a battery 108 by measuring the voltage drop when the discharge load is applied (the series resistance is a measure of the health of the rechargeable battery 108); the ability to test a voltage and a current of the rechargeable battery 108 by comparing its readings with the battery conditioning system's 100 readings while the discharge load is applied.

WCD monitors 30 of the present disclosure may include a battery, which may be removable and may be rechargeable. Generally, the battery may releasably lock to the WCD monitor 30 through one or more locking mechanisms, including two-button mechanisms, single-button mechanisms, and additional mechanisms described below.

FIGS. 12-20 illustrate a WCD monitor battery 200 featuring a latch-and-handle mechanism 204, the battery 200 being particularly suitable for use when the WCD monitor user suffers from arthritis, degraded vision, and/or reduced dexterity. The battery 200 is designed to be easily removable from the WCD monitor 30. At the same time, the battery 200 engages securely with the WCD monitor 30 and will not disengage if the WCD monitor 30 is dropped or if a patient collapses on it while suffering cardiac arrest.

The mechanism 204 allows a user to quickly and easily locate the battery 200, unlatch it, and disengage it from the WCD monitor 30. The mechanism 204 includes pivots 208a, 208b and a handle 212 that may be rotated to disengage snap beams 220a, 220b from ramps (not shown). The handle 212 provides an easy hand-hold for gripping, and also provides a simple action to latch/unlatch the battery 200 from the WCD monitor 30.

Figure 20:
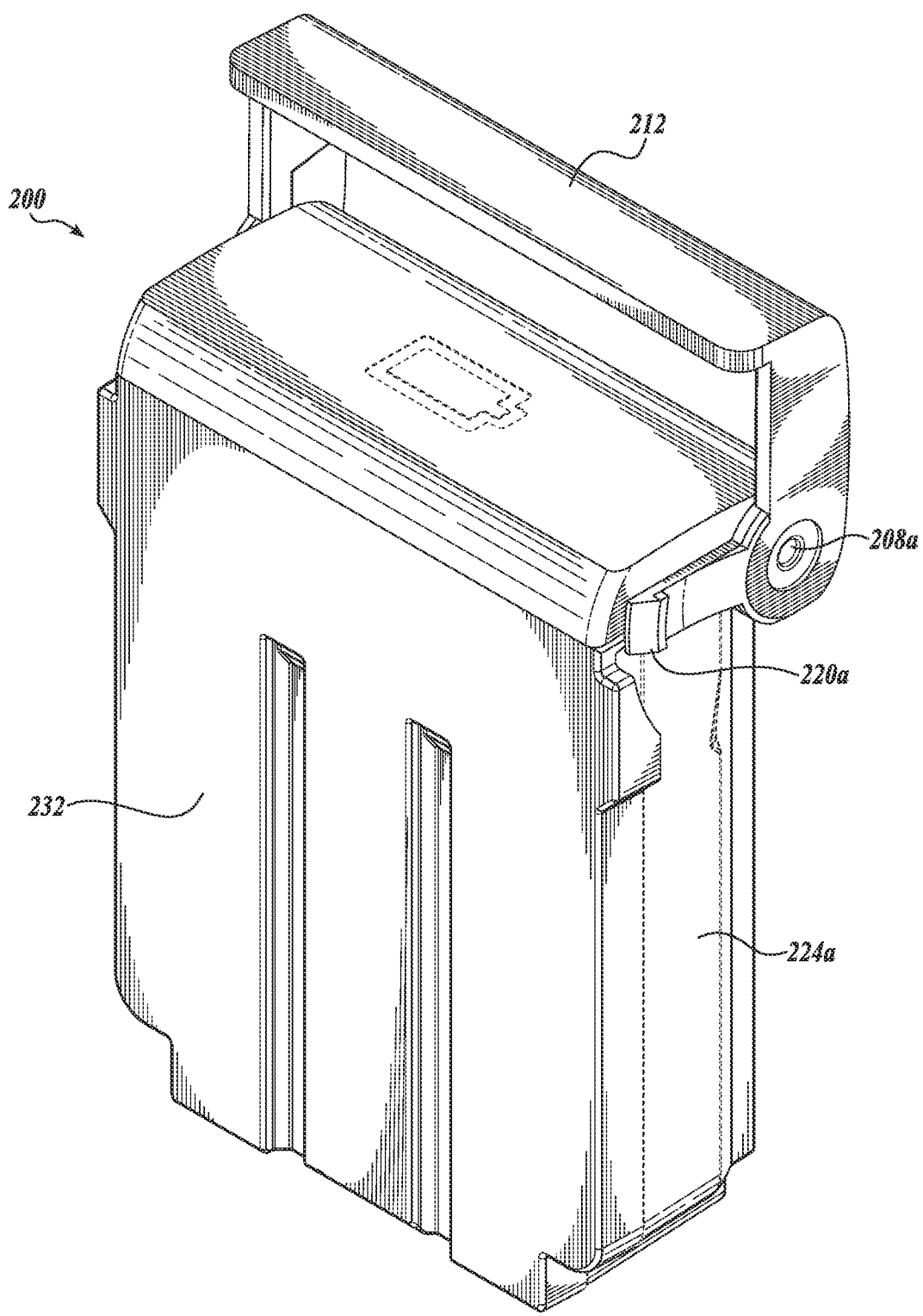
FIG. 20 is a third perspective view of the removable battery shown in FIG. 12, shown with the handle in an open position.

The handle 212 may pivot through an angular range (e.g., about 90 degrees) between a closed position as shown in FIGS. 12-19 and an open position as shown in FIG. 20. In the closed position, the handle 212 is folded down onto the battery 200 and snap beams 220a, 220b extend downward along sides 224a, 224b, respectively, toward a bottom surface 228 of the battery 200. In the open position shown in FIG. 20, the handle 212 extends away from the battery 200 and the snap beams 220a, 220b extend toward a front surface 232 of the battery 200.

The snap beams 220a, 220b each latch over ramps located in the WCD monitor 30 (ramps not shown) when the handle 212 is in the closed position and as long as the handle 212 remains below a threshold angle within the angular range between the closed position and the open position (e.g., about 30 degrees, about 45 degrees, about 60 degrees, etc.). The ramps may be located on the housing 38 or another part of the WCD monitor 30. So long as the snap beams 220a, 220b remain engaged with the ramps, the battery 200 cannot easily be removed from the WCD monitor 30. When the handle 212 is rotated away from the battery 200 beyond the threshold angle, the snap beams 220a, 220b rotate away from their respective ramps. Subsequently, the battery 200 may be removed from the WCD monitor 30 by pulling on the handle 212. The handle 212 may be spring loaded to bias the handle toward the closed position.

In another embodiment, the battery 200 may utilize a cylindrical cam and rocker arm mechanism that is similar to the snap beam embodiment described above, but utilizes a cylindrical cam adjacent to the battery handle 212 as an actuator to push a latch paw, which may in turn engage the WCD monitor 30. The latch paw may be spring loaded against movement of the handle 212 to bias the latch paw toward an engaged position.

The WCD monitor 30 may use an optional secondary latch (not shown) to hold the snap beams 220a, 220b in the closed position until the handle 212 is rotated. This secondary latch can be a spring plunger that retracts during insertion of the battery 200 into the WCD monitor 30, and then springs back behind the snap beams 220a, 220b when they engage their respective ramps, thereby locking the snap beams 220a, 220b in engagement with the ramps. The snap beams 220a, 220b may not be disengaged from the ramps until the spring plunger is depressed, such as by rotation of the handle 212, pressing of a button (not shown), or other action.

In another embodiment, the battery 200 utilizes a linkage and slider mechanism to secure the battery 200 within the WCD monitor 30. This embodiment utilizes a mechanical linkage to convert rotational movement of the handle 212 into linear motion of a slider, which causes a latch paw (housed inside the battery 200) to engage the WCD monitor 30. In such embodiments, the battery 200 can be unlatched by rotating the handle 212 towards the open position beyond a threshold angle (e.g., about 45-60 degrees), thereby retracting the latch paw and disengaging the WCD monitor 30. Subsequently, the battery 200 can be removed from the WCD monitor 30 with by pulling on the handle 212.

In another embodiment, the battery 200 may utilize a pulley and slider mechanism to secure the battery 200 within the WCD monitor 30. This embodiment utilizes a similar principle as the linkage-and-slider mechanism discussed above, but instead of a rigid mechanical linkage, utilizes a flexible string or cord that is anchored to the handle 212 and a sliding member to release a latch paw.

In order to provide valuable diagnostic information for physicians in the case of a cardiac event, a WCD system may include a subsystem for storing relatively large amounts of ECG data and event data in a data store. This data may also be transmitted over a wired or wireless communications interface to a location accessible from the internet. One non-limiting method of transferring this data to the internet is to have the patient carry an assistant device (such as a customized cell phone) that communicates with the WCD system over a wired or wireless communications interface. For example, the assistant device may be a cell phone that communicates with the WCD system over a low power Bluetooth connection, and then uses a cellular connection to transmit data to a server on the internet. This assistant device could also be used as an auxiliary user interface between the WCD and the patient to present more detailed information about the device status and even request input from the patient.

As used in this disclosure, a data store is a tangible machine-readable storage medium that includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.). As used in this disclosure the communications interface may have circuits configured to enable communication with remote server, base station, or other network element via the internet, cellular network, RF network, Personal Area Network (PAN), Local Area Network, Wide Area Network, or other network. Accordingly, the communications interface may be configured to communicate using wireless protocols (e.g., WIFI®, WIMAX®, BLUETOOTH®, ZIGBEE®, Cellular, Infrared, Nearfield, etc.) and/or wired protocols (Universal Serial Bus or other serial communications such as RS-234, RJ-45, etc., parallel communications bus, etc.). In some embodiments, the communications interface includes circuitry configured to initiate a discovery protocol that allows the WCD and other network element to identify each other and exchange control information. In an embodiment, the communications interface has circuitry configured to a discovery protocol and to negotiate one or more pre-shared keys. In an embodiment, the communications interface alternatively or additional includes circuitry configured to initiate a discovery protocol that allows an enterprise server and the WCD to exchange information.

Performing all this processing, data storage and data transmission takes a significant amount of power. A patient may be required to wear a wearable component of a WCD system for up to about 90 days so it may be impractical to use a battery large enough to last the entire period. Indeed, such a battery may be too large and heavy for the patient to carry. Therefore, a smaller rechargeable battery may be used as an alternative. WCD systems such as those of the present disclosure are typically powered by removable rechargeable batteries that utilize a battery charger (such as charger 116). In some embodiments, the battery charger may have the ability to test the WCD battery, to report performance failures and error conditions, and to alert the patient that they may need to call and request a new battery. In some embodiments, the battery charger may include a separate charging well (or a larger single charging well) intended to charge an assistant device (e.g., a cell phone or other hand held device) that provides an interface between the WCD system, the patient, and internet for other connections. This battery charger may provide a single location for the patient to recharge both the WCD battery and the assistant device (or assistant device battery) on a periodic (e.g., daily) basis. In such embodiments, the rechargeable battery should be removed from the WCD monitor and placed in a battery charger, ideally while the patient connects a second battery into the WCD. This recharge routine may occur daily, weekly, or on another periodic schedule.

This periodic routine is made more convenient for the patient if they can recharge the assistant device using the same charger as the WCD battery. To enable this, the battery charger may have two recharging wells: one for the WCD battery and one for the assistant device. In an embodiment, the recharger may include a single charging well sized large enough to accommodate the WCD battery and the assistant device (or assistant device battery). To add even more convenience, the assistant device charging well could be configured to wirelessly charge the assistant device, so that the patient does not have to plug in a cord. In such an embodiment, the patient could simply drop both the WCD battery and assistant device into the charging station.

In some embodiments of the battery charger, the charger recognizes that a WCD battery has been inserted into the charging well. Upon or after this recognition, the charger may execute one or more battery tests. Any combination of features from the following exemplary embodiments may be combined in any other embodiment described herein, and may be applied with respect to the WCD battery and/or the assistant device battery. In an embodiment, the WCD charger can assess the charge state of the WCD battery and if there is sufficient remaining capacity it can begin one or more tests on the battery. In an embodiment, it can apply a momentary load while monitoring the voltage to measure the series impedance of the battery. In an embodiment, while a load is applied, the battery charger can query the WCD battery for its measurements of voltage and current and compare them with its own to determine the accuracy of any battery measurement circuits. In an embodiment, the charger can read error logs and/or event logs and execute one or more other tests to verify the integrity of the WCD battery.

In an embodiment, any of the foregoing battery tests may be completed within a short time of the battery being inserted (e.g., within one minute, 30 seconds, 10 seconds, etc.), so that if an error condition or performance issue is detected, the patient will still be near the battery charger and can be alerted by a charger display and/or audio output so that the patient can call and request a new WCD battery. If the WCD battery is too low on capacity upon placement into/onto the battery charger to perform any tests, then the battery charger could charge the WCD battery for some time period and then perform the tests and display/announce the results.

Embodiments of the battery charger may include any single or combination of the following features: A USB charging port so that a phone or other USB device that is not wireless-charging enabled could be charged; a display, such as an LCD display, to present information about the WCD or assistant batteries and charger status; a visual indicator, such an LED light, to attract the patient's attention if an issue with any battery is discovered; an audio device, such as a speaker or buzzer, to draw attention for any of the above; the battery charger could be designed such that the WCD battery fits into the charging well in much the same way that it fits into the WCD itself, facilitating easier use for the patient; the assistant device charging well could be designed so that the assistant device's display remains visible, allowing it to present information to the patient even while it's charging.

One or more of these features of the WCD battery charger can be designed to make the experience of wearing one of these devices as easy and safe as possible. Being alerted to an issue with one of the batteries as soon as possible will minimize the amount of time a patient may have to go without their WCD device to protect them.

Embodiments of the WCD monitor 30, battery conditioning system 100, and battery 200 may include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or monitor, and/or the steps, acts, or modalities of a method.

While illustrative embodiments have been illustrated and described, it will be appreciated that various changes can be made therein without departing from the spirit and scope of the disclosure. It should be also understood that any block diagram, flowchart illustration, operational or method descriptions, or parts thereof, respectively, may be implemented in part by computer program instructions, e.g., as logical steps or operations executing on the the processor component. These computer program instructions may be loaded onto a computer, such as a special purpose computer or other programmable data processing apparatus, such as a processor unit, processor component, etc., to produce a specifically-configured machine, such that the instructions which execute on the computer or other programmable data processing apparatus implement the functions specified in any illustrated block or blocks, flowcharts, and/or the methods steps described herein in any combination, etc.

This patent may reference directions, e.g., front, rear, top, bottom, left, and right. These references are intended only to aid in understanding of the embodiments, and do not limit the orientation, location, position, of any feature of the embodiments, or otherwise limit the scope of the present disclosure.

This patent may also reference quantities and numbers. Unless specifically stated, such quantities and numbers are not to be considered restrictive, but exemplary of the possible quantities or numbers associated with the disclosure. Also in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The invention claimed is:

1. A method of servicing a wearable cardioverter defibrillator (WCD) monitor case, comprising:
   receiving a wearable cardioverter defibrillator monitor case, the wearable cardioverter defibrillator monitor case having:
      a housing configured to surround a defibrillator electronics assembly;
      a front cover removably attachable to the housing;
      a rear cover removably attachable to the housing; and
      a non-powered shock indicator positioned on the case at an interface between the housing and the front cover;
   removing the front cover from the housing; and
   attaching the front cover to the housing.

2. The method of claim 1, further comprising inspecting the shock indicator for a sign of a shock in excess of a shock threshold.

3. The method of claim 2, further comprising replacing the shock indicator.

4. The method of claim 1, further comprising removing the rear cover from the housing and attaching a replacement rear cover to the housing.

5. The method of claim 1, further comprising removing a defibrillator electronics assembly from the housing and functionally testing the defibrillator electronics assembly.

6. The method of claim 1, wherein the WCD monitor case is received from a first user.

7. The method of claim 6, further comprising providing the WCD monitor case to a second user, the first user being different from the second user.

8. The method of claim 5, wherein the method further comprises receiving with a remote device a signal from the defibrillator electronics assembly that a shock in excess of a shock threshold has occurred.

9. The method of claim 1, wherein the method further comprises inspecting the WCD monitor housing.

10. The method of claim 9, wherein inspecting the WCD monitor housing comprises a visual inspection.

11. The method of claim 9, wherein inspecting the WCD monitor housing comprises functionality testing a board stack of the WCD monitor housing.

12. The method of claim 9, wherein inspecting the WCD monitor housing comprises partially or completely disassembling the WCD monitor housing.

13. The method of claim 1, wherein the shock indicator is positioned within a recess.

14. The method of claim 1, wherein the shock indicator is a mechanical or chemical shock indicator.

15. The method of claim 1, wherein the front cover includes a window.

16. The method of claim 1, wherein the WCD monitor housing further comprises a second shock indicator, wherein the shock indicator and the second shock indicator are positioned on different components of the wearable cardioverter defibrillator monitor case.

17. The method of claim 16, wherein the method further comprises inspecting the shock indicator and the second shock indicator for a sign of a shock in excess of a shock threshold of the first shock indicator, the second shock indicator, or both.

18. The method of claim 16, wherein the method further comprises replacing the first shock indicator, the second shock indicator, or both.

* * * * *